United States Patent [19]

Zarchy

[11] Patent Number: 5,145,815
[45] Date of Patent: Sep. 8, 1992

[54] REGENERATION OF ZEOLITIC MOLECULAR SIEVES WITH SULFUR OXIDE ABSORPTION ON SODA-LIME BED

[75] Inventor: Andrew S. Zarchy, Amawalk, N.Y.

[73] Assignee: UOP, Des Plaines, Ill.

[21] Appl. No.: 746,837

[22] Filed: Aug. 19, 1991

Related U.S. Application Data

[62] Division of Ser. No. 391,894, Aug. 10, 1989, Pat. No. 5,041,693.

[51] Int. Cl.$^5$ .............................. B01J 20/34
[52] U.S. Cl. .......................... 502/52; 55/73; 502/38; 502/400; 502/517
[58] Field of Search ............ 208/310 Z, 310 R; 585/826; 423/244 H; 502/38, 52, 517, 51, 400; 55/73

[56] References Cited

U.S. PATENT DOCUMENTS

| | | | |
|---|---|---|---|
| 3,422,005 | 1/1969 | Avery | 208/310 |
| 3,700,589 | 10/1972 | Symoniak et al. | 208/310 |
| 3,812,200 | 5/1974 | Grey et al. | 502/417 |
| 3,976,747 | 8/1976 | Shale et al. | 423/244 H |
| 4,176,053 | 11/1979 | Holcombe | 208/310 Z |
| 4,551,304 | 11/1985 | Holter et al. | 422/4 |
| 4,600,568 | 7/1986 | Yoon et al. | 423/242 |
| 4,604,269 | 8/1986 | Yoon | 423/242 A |

FOREIGN PATENT DOCUMENTS 903813  8/1962  United Kingdom ............ 208/310 Z Primary Examiner—Paul E. Konopka
Attorney, Agent, or Firm—Thomas K. McBride; John G. Tolomei; Richard P. Silverman

[57] ABSTRACT

Methods are provided for regenerating a zeolitic molecular sieve having a sulfur-containing carbonaceous material deposited thereon by contacting the zeolitic molecular sieve with an oxygen-containing regeneration feed gas to remove at least a portion of the carbonaceous deposit material and thereafter absorbing sulfur oxides present in the regeneration gas using soda-lime absorbent. The methods can inhibit the deactivation of zeolitic molecular sieves by avoiding contact thereof with the sulfur oxides.

10 Claims, No Drawings

REGENERATION OF ZEOLITIC MOLECULAR SIEVES WITH SULFUR OXIDE ABSORPTION ON SODA-LIME BED

CROSS-REFERENCE TO RELATED APPLICATIONS

This application is a division of U.S. Ser. No. 391,894, filed Aug. 10, 1989 and issued Aug. 20, 1991 as U.S. Pat. No. 5,041,693.

FIELD OF THE INVENTION

The present invention relates generally to the oxidative regeneration of zeolitic molecular sieves and more particularly to methods for inhibiting the deactivation of zeolitic molecular sieves used in processing sulfur-containing hydrocarbon feeds wherein the deactivation is caused by exposure to sulfur oxides formed during oxidative regeneration of the molecular sieves.

BACKGROUND OF THE INVENTION

Zeolitic molecular sieves have been utilized in a variety of catalytic and adsorption processes. When the molecular sieves are used to process hydrocarbon feeds, often after a period of use, a carbonaceous deposit material forms on the molecular sieve which imparts some loss of activity. Usually, the activity can be at least partially restored by performing an oxidative regeneration which removes a portion of the carbonaceous deposit material from the molecular sieve.

When the hydrocarbon feeds contain sulfur compounds, the carbonaceous deposit material that forms on the molecular sieve can also contain sulfur. Upon oxidative regeneration, the sulfur is converted to sulfur oxides, i.e., primarily $SO_2$ and some $SO_3$, and expelled from the zeolitic molecular sieve with the regeneration gas. Since it is often advantageous to recycle the regeneration gas through the molecular sieve in a closed loop, these sulfur oxides are repeatedly contacted with the molecular sieve.

Despite the restorative effect of the oxidative regeneration with respect to the carbonaceous deposit material, it has been observed that repeated contact with sulfur oxides can cause permanent deactivation of the molecular sieve. It appears that during regeneration, the $SO_2$ is further oxidized to $SO_3$ at the relatively high regeneration temperatures, i.e., typically, 750°–1000° F., when contacted with the zeolitic molecular sieves. The $SO_3$ then apparently irreversibly reacts with the molecular sieve and causes the above-described deactivation. The exact mechanism of the deactivation is not known although it is generally observed as either a loss in adsorptive capacity or a loss in catalytic activity.

This problem can be encountered in essentially any catalytic or adsorption processes that utilize zeolitic molecular sieves to process sulfur-containing hydrocarbon feeds and which may be adversely affected by exposure to sulfur oxides during oxidative regenerations.

For instance, U.S. Pat. Nos. 3,700,589 and 4,176,053 describe processes for separating normal paraffins from non-normal paraffins in vapor phase using a fixed adsorption bed containing 5A zeolitic molecular sieve adsorbent. The hydrocarbon streams treated in accordance with the above-identified patents consist essentially of mixtures of branched chain paraffins and normal paraffins boiling in the gasoline and kerosene ranges. Such mixtures occur as petroleum naphthas, both light and heavy, natural gasolines and natural gas condensates, but also can be the products of processes outside the petroleum production and refining industry. In general, the hydrocarbons of these streams contain from about 4 to about 13 carbon atoms and can contain sulfur compound impurities typically in a concentration of less than 400 ppmv. The processes of the above-identified patents provide for an oxidative regeneration to remove carbonaceous deposit material that gradually accumulates on the adsorbent and causes a reduction in adsorption capacity, but do not specifically provide for the removal of sulfur oxides formed during the regeneration process.

Another patent, U.S. Pat. No. 3,422,005 describes a separation process for separating normal paraffins from a hydrocarbon vapor feed stream having 10 to 25 carbon atoms per molecule using normal hexane purge and zeolitic molecular sieve adsorbent. This carbon range covers both kerosene and gas oil feeds which have ASTM boiling ranges of from about 275°–600° F. and about 400°–700° F., respectively and commonly contain sulfur compounds in concentrations as high as 3000 ppmv.

In view of the fact that sulfur oxides can cause permanent deactivation of zeolitic molecular sieves during oxidative regenerations, despite the fact that the organic sulfur compounds typically present in the hydrocarbon feeds apparently do not cause permanent deactivation, it can be appreciated that it would be advantageous to remove sulfur oxides from regeneration gas before recycling it to the molecular sieve.

There are a variety of well known processes for removing sulfur oxides from gaseous streams. For example, in flue gas desulfurization, wet scrubbing processes have been employed wherein the flue gas is contacted with an aqueous solution of an organic acid to form a soluble sulfite or sulfate which is thereafter removed from solution by reaction with a calcium compound such as calcium hydroxide. Other flue gas desulfurization processes, such as described in U.S. Pat. Nos. 4,600,568 and 4,604,269, involve spraying a dry absorbent, such as slaked lime, into a flue gas stream along with an aqueous solution containing a solubilizing agent and thereafter removing the loaded absorbent by using a bag filter or electrostatic precipitator. While the above-identified methods are effective, they are far too complex for the purposes of the present invention.

U.S. Pat. No. 4,551,304 describes a method of purifying air loaded with pollutants, such as sulfur dioxide, nitrogen dioxide, nitrogen oxide and hydrocarbon compounds, wherein soda-lime absorbent is used to remove the acid gases from the air. The patent discloses the preferred initial step of ozonizing the air to convert $SO_2$ to $SO_3$ or NO to $NO_2$, such converted compounds being more readily absorbed on the soda-lime.

U.S. Pat. No. 3,812,200 discloses a process for the reactivation of a soda-lime absorber bed used for removal of $H_2S$ and $CO_2$ from normally gaseous hydrocarbons, i.e., propane and propylene, by injecting steam into the bed after it has reached its capacity. The above-identified patent discloses that after steam reactivation, the absorber can be utilized again to have more than 50% additional on-stream time.

None of the above-identified sulfur removal processes specifically address the problem of inhibiting deactivation of zeolitic molecular sieves by removing sulfur oxides from the regeneration gas streams. Accordingly, methods are sought for the regeneration of zeolitic molecular sieves having a sulfur-containing carbonaceous material deposited thereon wherein sulfur oxides are removed prior to contacting with the molecular sieves in order to inhibit deactivation thereof.

SUMMARY OF THE INVENTION

The present invention provides methods for the regeneration of zeolitic molecular sieves having a sulfur-containing carbonaceous material deposited thereon wherein sulfur oxides are removed prior to contacting with the molecular sieves. The method of the present invention is particularly suitable for inhibiting the deactivation of a zeolitic molecular sieve used in processing a sulfur-containing hydrocarbon feed wherein the deactivation is caused by exposure to sulfur oxides formed during the oxidative regeneration of the zeolitic molecular sieve. The method includes contacting the zeolitic molecular sieve with an oxygen-containing regeneration feed gas to remove at least a portion of the carbonaceous deposit material and form a first regeneration effluent gas containing sulfur oxides, i.e., $SO_2$, $SO_3$ and $H_2O$. The first regeneration effluent gas is then preferably cooled and flashed to remove excess $H_2O$ then contacted with a solid absorbent material comprising soda-lime to absorb at least a portion of the sulfur oxides. Prior to contacting the first regeneration effluent gas with the solid absorbent, an oxygen content sufficient to cause the absorption of the sulfur oxides is established in the first regeneration effluent gas. This can be accomplished by admixing an oxygen-containing stream with the gas. A second regeneration effluent gas depleted in sulfur oxides is then recovered and recycled for further contacting with the zeolitic molecular sieve.

The sulfur-containing carbonaceous material is formed as a by-product of a processing step wherein a sulfur-containing hydrocarbon feed is contacted with a zeolitic molecular sieve to produce at least one desired product. The above-mentioned processing step and the hydrocarbon feed and desired products associated therewith are not a critical aspect of the present invention. In some instances, the contacting may be continuous and be performed until it is desired to regenerate the molecular sieve. In other instances, the contacting may be discontinuous, or cyclic as in many adsorption-desorption processes, in which case the discontinuous contacting may be performed repeatedly before it is desired to regenerate the molecular sieve.

In a specific aspect of the present invention, a method is provided for separating normal paraffins from a sulfur-containing hydrocarbon feed comprising a mixture of normal paraffins having from about 10 to about 25 carbon atoms per molecule and non-normal hydrocarbons. The feed is passed to an adsorber bed containing a zeolitic molecular sieve having a pore size of about 5 Angstroms at a temperature of about 500°-800° F. and a pressure from about 20 to about 65 psia to adsorb the normal paraffins from the feed and produce an adsorption effluent product containing the non-normal hydrocarbons which is then withdrawn from the adsorber bed. After the adsorption effluent has been recovered, the bed is then desorbed by passing a purge stream containing normal hexane through the adsorber bed and a desorption effluent containing normal hydrocarbons is then recovered from the adsorber bed. This adsorption-desorption process is continued until a desired level of carbonaceous deposit material is formed on the molecular sieve, then an oxygen-containing regeneration feed gas is passed through the adsorber bed at a temperature of from about 750° to about 1000° F. to remove at least a portion of the carbonaceous deposit material from the molecular sieve. A first regeneration effluent gas containing $SO_2$ and $H_2O$ is removed from the adsorber bed, preferably cooled and flashed to remove excess water therefrom, and passed through an adsorber bed containing soda-lime to absorb at least a portion of the $SO_2$, wherein prior to said passing, an oxygen content sufficient to cause absorption of the $SO_2$ is established in the first regeneration effluent gas. A second regeneration effluent gas depleted in $SO_2$ is withdrawn from the absorber bed and at least a portion of it is recycled back to the zeolitic molecular sieve to provide at least a portion of the regeneration feed gas.

DETAILED DESCRIPTION OF THE INVENTION

The present invention relates to the regeneration of zeolitic molecular sieves that have a sulfur-containing carbonaceous material deposited thereon. The process of the present invention incorporates the use of a solid adsorbent that comprises soda-lime, and preferably, consists essentially of soda-lime, to remove sulfur oxides from the regeneration gas loop.

The term "soda-lime," as used herein, is defined as lime which has added thereto sodium hydroxide and sometimes is described as a mixture of "soda and lime." The mixture should be in pellet form of from 5 to 20 mesh size, preferably, 8–12 mesh. The term "lime" includes quick-lime and hydrated-lime. Lime can be prepared from limestone which is a rock composed of at least 50% calcium carbonate with varying percentages of impurities present. Limestone in its broadest sense includes any calcium containing material such as marble, chalk, travertine, coral, etc. These limes may contain from 5–45% magnesium carbonate. Usually, however, limestone refers to stratified calcareous rock composed mainly of the mineral calcite. Upon calcination, limestone yields the lime of commerce.

The calcination of limestone, under carefully controlled conditions, drives off carbon dioxide leaving primarily calcium oxide and magnesium oxide, otherwise known as quicklime. Treating quicklime with enough water to satisfy its chemical affinity for water produces a dry powder known as hydrated-lime. Hydrated-lime is essentially calcium hydroxide or a mixture of calcium hydroxide, magnesium oxide, and magnesium hydroxide.

The soda-lime of the present invention consists of lime obtained, as above described, which has added thereto a minor amount of sodium hydroxide. The amount of sodium hydroxide calculated as sodium may vary from 1–10% but preferably from 2–4%. The soda-lime may contain minor amounts of potassium. A typical sample of soda-lime used herein for illustration purposes, contains from 2.5–3.2% sodium hydroxide calculated as sodium with the remainder being calcium hydroxide, a small amount of potassium hydroxide, and water, either as water of hydration or free moisture. The water hydration may amount to 14–18% with the free moisture content varying between 0.5–5%. The soda-lime used in this invention is a commercially available commodity.

A typical regeneration gas loop comprises a recirculating gas stream having an oxygen content from about 0.1 to about 10 mol %, preferably, from about 0.5 to about 3 mol % with the balance comprising an inert gas such as nitrogen. The temperature of the regeneration gas contacting must be sufficient for the removal of the carbonaceous deposit material from the molecular sieve. This temperature is generally in the range of from about 750° to about 1000° F. and should not exceed a temperature in excess of about 1300° F. as this can cause internal damage to the crystal structure of the molecular sieve. The effluent from the molecular sieve bed, i.e., hereinafter denoted as first regeneration effluent gas, typically contains little or no oxygen since oxygen is consumed in the combustion. It does, however, contain sulfur oxides and other combustion products such as $H_2O$ and $CO_2$. The amounts of $H_2O$ and $CO_2$ present in the first regeneration effluent gas are generally within the range of from about 1 to about 20 mol. %. Preferably, the first regeneration effluent gas is cooled and flashed to remove excess $H_2O$ and prevent a build-up of $H_2O$ in the recirculating gas. The $H_2O$ content after flashing is preferably its saturation content at flashing conditions, e.g., 2.7 mol. % at 100° F., 35 psia, and typically within the range of from about 0.1 to about 4 mol. %. The balance of the first regeneration gas effluent typically consists essentially of the inert gas component, e.g., nitrogen, but may contain small amounts of other components such as CO, COS, $CH_3SH$, $H_2S$ or $H_2$. The sulfur oxide content present in the first regeneration effluent gas is typically from about 100 to 1000 ppmv and is primarily comprised of $SO_2$ although there may be small amounts of $SO_3$ present.

The first regeneration gas effluent is then passed through the absorber bed which contains soda-lime absorbent. The exact conditions required to absorb the sulfur oxides from the first regeneration effluent gas are not critical to the process of the present invention although typically the temperature will range from about 80° to about 180° F. It is important, however, that the first regeneration effluent gas comprise a sufficient quantity of $H_2O$ and $O_2$ to enhance the adsorption of the sulfur oxides on the soda-lime. Without these components, the soda-lime has insufficient selectivity for sulfur oxides especially when large amounts of $CO_2$ are present in the gas stream. It is often required, therefore, to admix the first regeneration effluent gas with an oxygen-containing stream prior to contacting with the soda-lime absorbent. The oxygen content must be sufficient to cause the absorption of at least a portion of the sulfur oxides. While not wishing to be bound to any particular theory, it appears that soda-lime in the presence of $O_2$ and $H_2O$ has the ability to catalyze the oxidation of the $SO_2$ to $SO_3$. The $SO_3$ then readily reacts with the soda-lime even in excess of $CO_2$ stoichiometrically. Accordingly, it is believed the amount of oxygen required can be as little as the stoichiometric amount required by the chemical equation:

$$SO_2 + \tfrac{1}{2}O_2 \to SO_3$$

However, it is generally desirable to provide an excess of oxygen. Accordingly, in a preferred aspect of the present invention, the first effluent regeneration gas contains from about 0.1 to about 3 mol % $O_2$.

The following table sets forth data which illustrates the adsorptive capacity of soda-lime when various gas components are present.

| Capacity | Feed Component Concentration (balance $N_2$) | | | | Wt. % of $SO_2$ |
|---|---|---|---|---|---|
| $SO_2$ | | $O_2$ | $H_2O$ | $CO_2$ | |
| 400 ppmv | | — | — | — | 5 |
| 400 ppmv | | — | 1.7 mol % | — | 30 |
| 200 ppmv | | — | 1.7 mol % | 15 mol % | 15 |
| 180 ppmv | | 2.1 mol % | 1.7 mol % | 13.5 mol % | 58 |

The data presented in the above table quite unexpectedly show that a substantial increase in the $SO_2$ capacity of the soda-lime when water was added to the gas stream, i.e., from less than 5 to about 30 wt. %. Moreover, when oxygen was added, the capacity was likewise substantially increased, i.e., from 30 wt. % to about 58 wt. %.

The amount of $SO_2$ remaining in the regeneration gas stream after contacting with the soda-lime will generally be very low during the initial stages of the absorption and will gradually increase as the capacity of the soda-lime for the $SO_2$ is exceeded. It is preferred that in the practice of the present invention, the $SO_2$ concentration in the effluent from the soda-lime absorber, i.e., the second regeneration effluent gas, be maintained in a range from about 0 to about 50 ppmv. It is also preferred that the second regeneration effluent gas be substantially free of $SO_3$. Once the capacity of the soda-lime absorbent has been reached, as determined by the sulfur oxide effluent concentration, for example, the gas flow through the absorber bed is terminated and the soda-lime absorbent is replaced. While it may be possible to at least partially regenerate soda-lime, as indicated in hereinbefore described U.S. Pat. No. 3,812,200, the preferred method for purposes of the present invention is to replace the spent soda-lime absorbent with fresh, or active, soda-lime absorbent. The size and number of soda-lime absorbed beds required for a particular application can be readily determined by those skilled in the art and need not be further described herein.

The sulfur-containing carbonaceous material is formed as a by-product of a processing step wherein a sulfur-containing hydrocarbon feed is contacted with a zeolitic molecular sieve to produce at least one desired product. The above-mentioned processing step and the hydrocarbon feed and desired products associated therewith are not a critical aspect of the present invention. In some instances, the contacting may be continuous and be performed until it is desired to regenerate the molecular sieve. In other instances, the contacting may be discontinuous, or cyclic as in many adsorption-desorption processes, in which case the discontinuous contacting may be performed repeatedly before it is desired to regenerate the molecular sieve.

The sulfur-containing hydrocarbon feeds used in the present invention are typically derived from refinery, natural gas or petrochemical sources and can range from light normally gaseous hydrocarbons such as propane and propylene which can contain $H_2S$ and COS to mid-range naphtha having 4 to 10 carbon atoms per molecule to much heavier kerosene or gas oil hydrocarbons both of which can contain a variety of mercaptans, sulfides and thiophenes.

Kerosene may be broadly defined as a hydrocarbon mixture having an initial boiling point, according to the American Society of Testing Materials (ASTM), of about 275° F. and an ASTM final boiling point below 600° F. Kerosene generally contains between about 10 and 40 mol % normal paraffins having 10 to 15 carbon atoms per molecule; these particular normal paraffins are typically used as raw materials for "biologically soft" detergents, industrial solvents and for the production of chlorinated petroleum waxes, lubricants, plasticizers, flame proofing agents and vegetable oils. The presence of non-normal hydrocarbons, such as isomers and aromatics, often have a detrimental effect on these products. Conversely, isomer hydrocarbons having 10 to 15 carbon atoms per molecule, as found in kerosene, are often used as jet fuel components and the presence of normal hydrocarbons adversely effects the freezing point of such fuels.

Gas oil may be broadly defined as a hydrocarbon mixture having an initial boiling point, according to the ASTM, of above 400° F. and an ASTM final boiling point below 700° F. Gas oil generally contains between about 10 and 40 mol % normal paraffins having 16 to 25 carbon atoms; these particular normal paraffins are typically used as raw materials for the synthesis of proteins, plasticizers and alcohols.

The zeolitic molecular sieves suitable for use in the present invention are three-dimensional crystalline aluminosilicates which in the calcined form may be represented by the general formula:

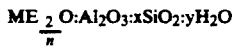

$$\frac{ME_2}{n}O:Al_2O_3:xSiO_2:yH_2O$$

where Me is a cation, x has a value from about 2 to infinity and y has a value of from about 2 to 10.

Typical well known zeolites which may be used include, chabazite, also referred to as Zeolite D, clinoptilolite, erionite, faujasite, also referred to as Zeolite X and Zeolite Y, ferrierite, mordenite, Zeolite A and Zeolite P. Detailed descriptions of the above-identified zeolites, as well as others, may be found in D. W. Breck, *Zeolite Molecular Sieves*, John Wiley and Sons, New York, 1974, hereby incorporated by reference. Other zeolites suitable for use, according to the present invention, are those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicalite disclosed in U.S. Pat. No. 4,104,294, hereby incorporated by reference.

In a specific aspect of the present invention, the above-described method for regenerating zeolitic molecular sieves is integrated into an adsorption process for the separation of normal paraffins from a hydrocarbon feed in the kerosene or gas oil range, i.e., from about 10 to about 25 carbon atoms per molecule and non-normal hydrocarbons. As the present invention provides a method for regenerating zeolitic molecular sieves, the details of the adsorption process used in separating the normal paraffins from the hydrocarbon feed are not critical to the invention and are well known to those skilled in the art. However, in general, the process is performed in a cyclical nature and includes the steps of passing the feed to an adsorber bed containing a zeolitic molecular sieve having the pore size of about 5 Angstroms, preferably, the calcium-exchanged form of Zeolite A in the form of 1/16" pellets. The temperature used for adsorption can vary but is generally in the range of from about 500° to about 800° F. and the pressure is generally from about 20 to about 65 psia for a kerosene or gas oil feedstock. As adsorption is continued, normal paraffins from the feed are adsorbed on the molecular sieve and an adsorption effluent containing nonnormals is withdrawn from the effluent end of the adsorber. The adsorption step is then terminated at a predetermined point, preferably, before substantial breakthrough of the adsorbed normal paraffins has occurred. Often after the adsorption step described above, a cocurrent purge comprising normal hexane is passed through the adsorber bed to displace hydrocarbon feed remaining in the void spaces of the adsorbent at the end of adsorption. When a cocurrent purge step is used, it should be terminated before a substantial amount of normal paraffins have desorbed from the adsorber bed.

At the conclusion of the cocurrent purge step, a countercurrent purge step using normal hexane is commonly employed to desorb normal paraffins from the adsorbent. A desorption effluent comprising normal paraffins and hexane is withdrawn from the adsorber bed and then separated into the hexane and normal paraffin components. The normal hexane recovered from the desorption effluent is then recycled along with normal hexane recovered from the above described adsorption effluent to be used again for desorption and optionally for cocurrent purge. A more detailed description of this adsorption cycle can be found in U.S. Pat. Nos. 3,422,005; 4,354,929 and 4,374,022.

As the adsorber beds are cycled at the operating temperature, the carbonaceous deposit material gradually accumulates. This deposit reduces the capacity of the adsorbent which can result in a breakthrough of a normal paraffins into the adsorption effluent product and hence can cause decreased normal paraffin recovery. The rate at which this deposit accumulates depends on factors such as temperature, feed impurities, feed properties, cycle time and residual paraffin loadings. This type of adsorbent deactivation is temporary so that the original bed capacity can be substantially restored by burning off this deposit under controlled conditions.

Oxidative regeneration is particularly suitable for this purpose. When the adsorber beds have been cycled until a desired level of carbonaceous deposit material has formed on the zeolitic molecular sieve, the normal process cycle is terminated and the regeneration method is commenced. In this specific aspect of the present invention, it is generally desirable to perform the oxidative regeneration when the level of carbonaceous deposit material that is formed on the zeolitic molecular sieve is from about 1 to about 10 wt. %. The oxidative regeneration procedure is preferably performed as follows. Circulation of an inert gas, such as nitrogen, is established by means of a recirculating flow scheme which provides a compressor and heating means which may or may not be part of the adsorption-desorption process flow scheme. The circulation of the inert gas has two purposes; namely, to remove as much of the residual normal paraffins as possible and to raise the temperature of the bed to above the coke ignition point prior to the introduction of oxygen into the stream. The effluent gas from the adsorber bed is preferably cooled to condense any hydrocarbons and water that may be desorbed. When the adsorber bed is heated to temperature of about 750° F., air is introduced into the circulating stream at a rate such that the oxygen content of the gas entering the bed is between about 0.1 and 10% by volume, preferably, between about 0.1 and 3% by volume. The oxygen in the gas combusts with the carbonaceous deposit material in the adsorber bed. The heat release from the combustion is carried out of the burning zone as a preheat front traveling ahead of the burning front. This preheat front raises the temperature to from about 750° to about 1000° F. This temperature is controlled by regulating the amount of oxygen in the entering gas. The regeneration gas effluent from the adsorber bed, as hereinbefore described, is cooled and flashed to remove excess water admixed with air in order to provide a sufficient oxygen content to cause absorption of the sulfur oxides, i.e., from about 0.1 to about 3 mol. %, and then passed to the soda-lime absorber to remove sulfur oxides therefrom. At least a portion of the effluent from the soda-lime absorbed is recycled for further use as regeneration gas. Preferably, the sulfur oxide-depleted regeneration gas is combined with air as required to provide make-up oxygen. The regeneration is continued until sufficient adsorptive capacity has been restored, which typically coicides with a level of carbonaceous deposit material of less than 1 wt. %, after which the adsorption process is resumed.

It shall be understood that there are other variations of the above-described methods which are embodied in the scope of the claims that follow. For example, the method of the present invention is equally applicable to moving bed or fluidized bed catalytic and adsorption processes wherein zeolitic molecular sieve is transported from the adsorption or reaction zone to a separate regeneration zone and transported back to the adsorption or reaction zone when regeneration is complete.

What is claimed is:

1. A method for regenerating a zeolitic molecular sieve having a sulfur-containing carbonaceous material deposited thereon, said method comprising:
    (a) contacting the zeolitic molecular sieve with an oxygen-containing regeneration feed gas to remove at least a portion of said carbonaceous deposit material and withdrawing a first regeneration effluent gas depleted in oxygen and comprising at least one sulfur oxide and $H_2O$;
    (b) contacting said first regeneration effluent gas in an absorbent bed with a solid particulate absorbent material comprising soda-lime, containing from 2 to 4 wt. % sodium hyhroxide, wherein prior to said contacting with said absorbent material said first regeneration effluent gas is admixed with an oxygen containing gas to raise the oxygen content of said first regeneration effluent gas to 0.1 to 3 mol. % which is sufficient to cause the absorption of at least a portion of said at least one sulfur oxide in said absorber bed and withdrawing a second regeneration effluent gas depleted in sulfur oxide from said absorber bed; and,
    (c) recycling at least a portion of said second regeneration effluent gas to provide at least a portion of said oxygen-containing regeneration feed gas.

2. The method of claim 1 wherein the oxygen-containing regeneration feed gas contains from about 0.1 to about 10 mol % oxygen.

3. The method of claim 1 wherein the contacting of the zeolitic molecular sieve with said oxygen-containing regeneration feed gas is conducted at a temperature of from about 750° to about 1000° F.

4. The method of claim 1 wherein the first regeneration effluent gas is cooled to a temperature of about 80°–180° F. and flashed to remove excess $H_2O$ therefrom.

5. The method of claim 4 wherein the first regeneration effluent gas is saturated with $H_2O$ after said flashing.

6. The method of claim 1 wherein the first regeneration effluent gas contains at least one sulfur oxide selected from the group consisting of $SO_2$, $SO_3$ and mixtures thereof.

7. The method of claim 6 wherein the first regeneration effluent gas contains from about 100 to about 1000 ppmv $SO_2$.

8. The method of claim 7 wherein the second regeneration effluent gas contains from about 0 to about 50 ppmv $SO_2$.

9. The method of claim 6 wherein the first regeneration effluent gas contains $SO_3$.

10. The method of claim 9 wherein the second regeneration effluent gas is substantially free of $SO_3$.

* * * * *